United States Patent [19]

Wiezer et al.

[11] 4,405,735
[45] Sep. 20, 1983

[54] SUBSTITUTED DIAZASPIRODECANES, THEIR PREPARATION AND THEIR USE AS STABILIZERS FOR ORGANIC POLYMERS, AND THE POLYMERS THUS STABILIZED

[75] Inventors: Hartmut Wiezer, Gersthofen; Gerhard Pfahler, Augsburg; Helmut Korbanka, Adelsried, all of Fed. Rep. of Germany

[73] Assignee: Hoechst Aktiengesellschaft, Fed. Rep. of Germany

[21] Appl. No.: 345,250

[22] Filed: Feb. 3, 1982

[30] Foreign Application Priority Data

Feb. 7, 1981 [DE] Fed. Rep. of Germany ....... 3104294

[51] Int. Cl.³ .................... C07D 498/10; C08K 5/35; C08L 79/04
[52] U.S. Cl. ........................... 524/95; 524/101; 525/186; 528/361; 528/367; 546/19
[58] Field of Search ................ 524/95; 546/19; 528/361

[56] References Cited

U.S. PATENT DOCUMENTS

| | | | |
|---|---|---|---|
| 4,066,615 | 1/1978 | Murayama et al. | 524/95 |
| 4,107,139 | 8/1978 | Mayer et al. | 524/95 |
| 4,110,334 | 8/1978 | Mayer et al. | 524/95 |
| 4,191,684 | 3/1980 | Wiezer et al. | 524/95 |
| 4,220,773 | 9/1980 | Wiezer et al. | 546/19 |
| 4,247,449 | 1/1981 | Wiezer et al. | 524/95 |
| 4,263,505 | 4/1981 | Slongo et al. | 524/95 |
| 4,340,534 | 7/1982 | Wiezer et al. | 528/361 |

Primary Examiner—John Kight, III
Assistant Examiner—R. A. White
Attorney, Agent, or Firm—Connolly and Hutz

[57] ABSTRACT

Diazaspirodecanes of the general formulae

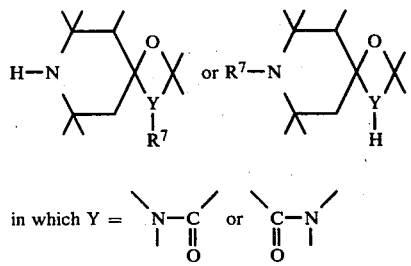

in which $Y = \underset{O}{\underset{\|}{\overset{}{\underset{|}{N-C}}}}$ or $\underset{O}{\underset{\|}{\overset{}{\underset{|}{C-N}}}}$ are reacted with epoxides or aldehydes to give alcohols and the latter are reacted with bifunctional compounds to form oligomers or polymers which can be used as light stabilizers for synthetic polymers. The alcohols can also be obtained if epoxy compounds which are substituted by the above diazaspirodecanes are converted into their formic acid esters and the latter are saponified.

4 Claims, No Drawings

SUBSTITUTED DIAZASPIRODECANES, THEIR PREPARATION AND THEIR USE AS STABILIZERS FOR ORGANIC POLYMERS, AND THE POLYMERS THUS STABILIZED

The present invention relates to compounds of the formula (I)

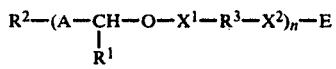   (I)

wherein n is an integer from 1 to 100, preferably from 1 to 50 and, in particular, from 1 to 20, $X^1$ and $X^2$ are either identical and represent a bond, a CO group or an —NHCO— group in which $R^3$ is attached to the nitrogen, or, if E has no meaning and n is 1, are different, in which case $X^2$ then has no meaning. $R^1$ represents hydrogen, $C_1$ to $C_{30}$ alkyl, preferably $C_1$ to $C_{18}$ alkyl, and in particular methyl, or represents phenyl, or represents, in particular, a group of the formula (IIa) or preferably (IIb)

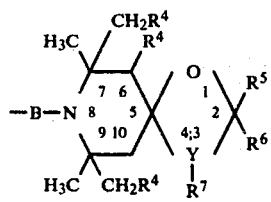

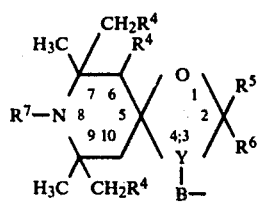

in which Y should be a radical

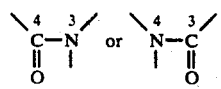

which occupies the ring positions 3;4.

B is a bond or a —CH$_2$— group, preferably the latter, and $R^4$ represents hydrogen or methyl, in particular hydrogen.

$R^5$ and $R^6$ are identical or different and denote hydrogen, $C_1$ to $C_{18}$ alkyl, preferably $C_1$ to $C_{13}$ alkyl and, in particular, $C_1$ to $C_9$ alkyl, phenyl which is unsubstituted or substituted by chlorine or $C_1$ to $C_4$ alkyl, or $C_7$ to $C_{14}$ aralkyl, preferably $C_7$ to $C_9$ phenylalkyl which is unsubstituted or substituted by $C_1$ to $C_4$ alkyl, or, together with the carbon atom linking these radicals represent a $C_5$ to $C_{12}$ cycloalkyl or piperidine ring which is unsubstituted or substituted by up to four $C_1$ to $C_4$ alkyl groups.

$R^7$ is hydrogen or $C_1$ to $C_4$ alkyl, preferably hydrogen.

If n is 1, $R^2$ represents hydrogen, a group of the formulae II, phenyl, $C_1$ to $C_{30}$ alkyl, preferably $C_1$ to $C_{18}$ alkyl, or an acyl or carbamoyl group which is substituted by $C_1$ to $C_{18}$ alkyl, by $C_5$ to $C_6$ cycloalkyl or by phenyl and in which the

group is attached to A, A then being a bond or —CH$_2$— or —CH$_2$O— in which the oxygen is attached to $R^2$, and, if A and B are a bond, $R^2$ preferably represents oxygen or methyl.

If n is 2, $R^2$ represents $C_2$ to $C_{18}$ alkylene, preferably $C_2$ to $C_{12}$ alkylene, phenylene which is unsubstituted or substituted by up to two $C_1$ to $C_4$ alkyl groups, preferably $C_1$ alkyl groups, α,ω-dicarboxy-$C_1$ to-$C_8$ alkylene, a dicarboxy-$C_6$ ring, $C_7$ to $C_{14}$ aralkylene, a radical >N-alkyl having 1 to 6 C atoms, or a group of the formula (III)

in which $R^5$ and $R^6$ have the meanings indicated above, and A then denotes —CH$_2$— or —OCH$_2$— in which —O— is attached to R$_2$, and, if R$_2$ is a group of the formula (III), A represents —CH$_2$—. If n is 3 and A as well as B represent a —CH$_2$— group, $R_2$ denotes an isocyanuric acid radical, a nitrogen atom or an

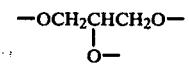

radical.

If $X^2$ and E have no meaning, $R^3$ is hydrogen, $C_1$ to $C_{18}$ alkyl, preferably $C_1$ to $C_{12}$ alkyl, phenyl which is unsubstituted or substituted by chlorine, hydroxyl, amino or $C_1$ to $C_4$ alkyl, $C_7$ to $C_{14}$ aralkyl, preferably phenylalkyl, or $C_5$ cycloalkyl or $C_6$ cycloalkyl, or represents $C_2$ to $C_{12}$ alkylene, phenylene which is unsubstituted or substituted by one to four $C_1$ to $C_4$ alkyl groups, preferably methyl groups, or represents $C_7$ to $C_{14}$ aralkylene, preferably $C_7$ to $C_9$ phenylalkylene.

A denotes in addition a group of the formula (IV)

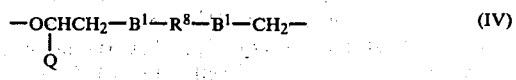

wherein Q represents a group of the formulae (II) in which B is —CH$_2$—, $B^1$ is a bond or oxygen, and $R^8$ denotes a bifunctional or trifunctional $R^2$ radical in which, if n is 3, the free valence is saturated by the group

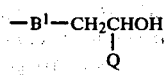

and —CH$_2$— is attached to $$-\underset{R^1}{CH}-.$$

A represents in addition a group of the formula

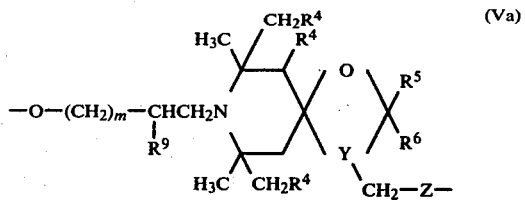
(Va)

in which $R^4$, $R^5$, $R^6$ and Y have the meanings indicated above, and Z is attached to —$CHR^1$— in formula (I) and represents a bond or —CH(OH)—. If m is O, $R^1$ in formula I has the meanings indicated above, $R^9$ is the same as $R^1$ and Z represents a bond.

If m is 1, $R^9$ represents an OH group, Z represents the group —CH(OH)— and $R^1$ in formula (I) represents hydrogen. If $R^1$ does not denote a group of the formulae (II), A also represents the groups of the formulae (Vb) or (Vc)

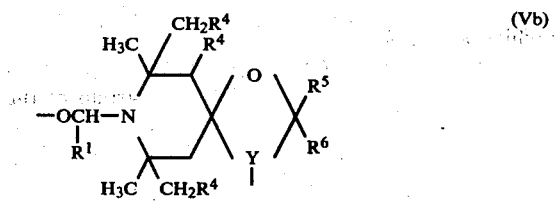
(Vb)

or

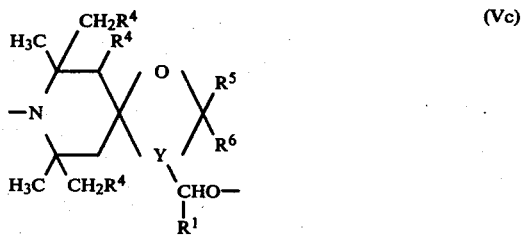
(Vc)

wherein $R^1$, $R^4$, $R^5$, $R^6$ and Y have the meanings indicated above, with the exception of $R^1$, which is a compound of the formulae (II), $R^1$ should preferably be hydrogen and the oxygen is attached to $R^2$. In oligomeric or polymeric products in which n>1, $R^2$, as a terminal group, is hydrogen, $R^3$ is a multifunctional radical, as indicated for n=2 or 3, and A has the meanings indicated for n=2 or 3. Finally, if n is 1, E denotes a group of the formula $R^2$—A—CH($R^1$)—O— wherein $R^1$, $R^2$ and A have the meanings indicated above for n=1, or E has no meaning or, as a terminal group for the case where n>1, E denotes a lower alkyl ester, preferably a methyl or ethyl ester, -NCO or halogen, preferably Cl, Br or I, $X^2$ then having no meaning. $R^2$, as a terminal group in the polymer, is hydrogen.

As least one of the radicals $R^1$, $R^2$ or A must contain a diazaspirodecane system of the formulae (II) or (V).

The new compounds are obtained from diazaspirodecanes of the general formulae (VI) which are described in German Offenlegungsschriften Nos. 2,606,026 and 2,634,957 (corresponding generally to U.S. Pat. Nos. 4,110,334 (Mayer et al) issued Aug. 29, 1978 and 4,107,139 (Mayer et al) issued Aug. 15, 1978)

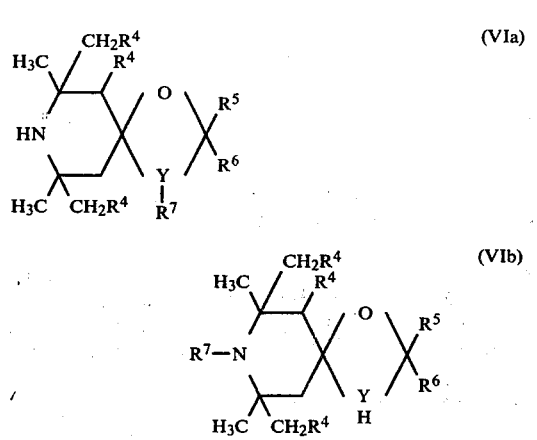
(VIa)

(VIb)

and wherein $R^4$, $R^5$, $R^6$, $R^7$ and Y have the meanings indicated above. This can be accomplished by following 2 routes.

Route (a) consists in reacting compounds (VIa) or (VIb), in the presence of catalysts, with 1.0 to 1.5 times, preferably 1.0 to 1.2 times, the equivalent quantity, in particular with the equivalent quantity, of an epoxide of the formula (VIIa)

(VIIa)

or with 1.0 to 3 times, preferably 1.0 to 1.5 times, the equivalent quantity, in particular with the equivalent quantity, of an aldehyde of the formula (VIIb)

$R^2$—(CHO)$_n$        (VIIb)

in which formulae (VII) $R^2$ has the meaning indicated above, n is an integer from 1 to 3 and D represents a bond or methylene or —OCH$_2$— in which —O— is attached to $R^2$. In formula (VIIa) $R^2$ additionally denotes a group of the formulae (II) in which B is a bond, in which case, in (VIIa), n is 1 and D is CH$_2$; thereafter in order to synthesize secondary products of a defined molecular weight, the alcohols thus obtained are, if desired, reacted with the equivalent quantity, in the case of polyols, in order to synthesize oligomeric or polymeric secondary products, reacted with the equimolar quantity, of a bifunctional compound of the formula (VIII)

$R^3$—(T)$_m$         (VIII)

in which $R^3$ has the meaning indicated above, m is an integer from 1 to 3 and T represents halogen, a lower alkyl ester, —COCl, —OH or —NCO.

In route (b), the starting materials are epoxy compounds of the formula (VIIa) wherein $R^2$ is a group of the formulae (IIa) or (IIb) in which B is a bond, D is —CH$_2$— and n is 1 (see German Offenlegungsschrift No. 2,834,962), and these compounds are reacted at 100°

C. with formic acid, which should be present in 3 to 10 times the molar quantity and acts at the same time as the solvent. The formic acid esters resulting from this reaction are then subjected to alkaline saponification by known methods to give the alcohol and, if desired, the latter is processed further as described in method (a) to give secondary products.

If the reaction route (a) is to be followed, the reaction is carried out, in the event of a compound of the formula (VIIa) being employed, in inert organic solvents, such as, for example, aliphatic alcohols in the presence of 0.1 to 2% by weight of a basic catalyst, it being preferable for 0.1 to 3% of a phase transfer catalyst to be present if the reaction is to take place at >Y—H, and for acid catalysts to be present if reaction at the basic >NH is desired. If a compound of the formula (VIIb) is to be reacted, basic catalysts are generally used, in the quantity indicated above, and it is then also possible to carry out the reaction in water. The reaction temperatures are between 50° and 180° C., preferably 70° and 160° C.

The conversion of the alcohols formed in this stage into secondary products is effected at temperatures of 80° to 180° C., preferably 100° to 160° C., in inert organic solvents, such as, for example, aromatic hydrocarbons, in the case where T=halogen with prior formation of the alkali metal alcoholate of the alcohols employed, in the case where T=lower alkyl ester using 0.1 to 0.5% by weight of a basic catalyst, such as, for example, $LiNH_2$, NaH, $NaOCH_3$ or $KOCH_3$, in the case where T=—NCO using 0.1 to 0.5% by weight of a basic catalyst, such as KOH or 1,4-diazabicyclo[2.2.2]octane, and in the case where T=—COCl using an equivalent quantity of a hydrogen halide acceptor. If alcohols obtained from (VIIb) are etherified, the reaction is carried out in the presence of acid catalysts, preferably using hydrogen chloride at a pH of approx. 2. No additional features are required for reaction route (b), the second part of which corresponds to the second part of reaction route (a).

The compounds disclosed in German Offenlegungschriften Nos. 2,606,026 and 2,634,957 (see the aforementioned U.S. Pat. Nos. 4,110,334 and 4,107,139, respectively), which in the present case are starting materials of the formula (VI) and which in themselves are already good stabilizers, are not entirely satisfactory, particularly as regards compatability with the polymers to be stabilized and as regards volatility. European patent application No. 17,617 also discloses compounds which are accessible from the starting materials mentioned above. These compounds are insufficiently effective because the center responsible for their activity as stabilizers is blocked in the case of the promising high-molecular products in which n>1. Stabilizers which contain other piperidine compounds as structural units and which constitute substances having an oligomeric structure are known from German Offenlegungsschrift No. 2,719,131 and European patent application No. 2,005. These products do not have an adequate light-stabilizing action. Accordingly, the new compounds surpass the stabilizers known from the above patent applications in all their properties, which could not have been expected. Furthermore, it could not have been expected that the reaction (a) in the preparation of the products would be so simple to control by a suitable choice of catalyst.

Examples of the compounds of the formulae (VI) which are used as starting materials are the diazaspirodecanes described in German Offenlegungsschriften Nos. 2,606,026, 2,634,957 (see U.S. Pat. Nos. 4,110,334 and 4,107,139, respectively) and 2,834,962 (corresponding substantially to U.S. Pat. No. 4,220,773 Wiezer et al, issued Sept. 2, 1980).

The following are examples of epoxides of the formula (VIIa): ethylene oxide, propylene oxide, glycidol, tris-(2,3-epoxypropyl) isocyanurate, 1,4-bis-(2,3-epoxypropoxy)-butane, di-(2,3-epoxypropyl) cyclohexane-1,2-dicarboxylate, di-(2,3-epoxypropyl) tetrahydrophthalate, bis-(2,3-epoxypropyl)-aminobutane, tris-(2,3-epoxypropyl)-amine, 2,3-bis-[4-(2,3-epoxypropyl)-phenyl]-propane, 5,5-dimethyl-1,3-[bis-(2,3-epoxypropyl)]-diazapentane-2,4-dione, epoxides such as are described in German Offenlegungsschrift No. 2,941,004 and 1,2,3,4-di-epoxybutane. Aldehydes of the formula (VIIb) have 1 to 12 C atoms. Formaldehyde and acetaldehyde may be mentioned preferentially.

The following are examples of compounds of the formula (VIII): bromobutane, dibromohexane, dibromodecane, iodomethane, ethyl acetate, methyl oenanthate, methyl laurate, methyl benzoate, diethyl malonate, diethyl succinate, diethyl adipate, dimethyl sebacate, dimethyl terephthalate, trimethyl benzene tricarboxylate, adipic acid dichloride, sebacic acid dichloride, cyclohexyl isocyanate, butyl isocyanate, octadecyl isocyanate, hexamethylene diisocyanate, p-tolyl isocyanate, phenyl isocyanate and 2,4-toluylene diisocyanate.

The new stabilizers can be incorporated without problems into the polymers to be stabilized and are excellently suitable for stabilizing the latter against oxidative degradation induced by light, that is to say damage of the polymers caused by the action of oxygen, heat and light. In addition to their excellent effectiveness as stabilizers, the new stabilizers are distinguished by their very good compatability with the polymers to be stabilized.

The following are examples of polymers which can be stabilized successfully: polymers derived from hydrocarbons with single or double unsaturation, for example polyolefins, such as polyethylene, which can optionally be crosslinked, polypropylene, polybut-1-ene, polyisobutene, polymethylbut-1-ene, polymethylpent-1-ene, polyisoprene, polybutadiene, polystyrene, copolymers of the monomers on which the said homopolymers are based, such as ethylene-propylene copolymers, propylene-but-1-ene copolymers, propylene-isobutene copolymers and styrene-butadiene copolymers, and terpolymers of ethylene and propylene with a diene, such as, for example, hexadiene, dicyclopentadiene or ethylidenenorbornene; mixtures of the above-mentioned homopolymers, such as, for example, mixtures of polypropylene and polyethylene, polypropylene and polybut-1-ene or polypropylene and polyisobutylene or mixtures of butadiene-acrylonitrile copolymers with a styrene-butadiene copolymer.

Vinyl polymers containing halogens, such as polyvinyl chloride, polyvinylidene chloride, polyvinyl fluoride, polychloroprene, chlorinated rubbers and copolymers of vinyl chloride and vinylidene chloride with one another and with other olefinically unsaturated monomers.

Polymers derived from α,β-unsaturated acids and derivatives thereof, such as polyacrylates and polymethacrylates, polyacrylamides and polyacrylonitrile and copolymers thereof with one another and with other vinyl compounds, such as acrylonitrile-butadiene-styrene copolymers, acrylonitrile-styrene copolymers and acrylonitrile-styrene-acrylic ester copolymers. Polymers derived from unsaturated alcohols and amines or acyl derivatives or acetals thereof, such as polyvinyl alcohol, polyvinyl acetate, stearate, benzoate or maleate, polyvinyl butyral, polyallyl phthalate or polyallylmelamine, and copolymers thereof with other vinyl compounds, such as ethylene-vinyl acetate copolymers. Homopolymers and copolymers derived from epoxides, such as polyethylene oxide, or the polymers which are derived from bisglycidyl ethers.

Polyacetals, such as polyoxymethylene and polyoxyethylene, and polyoxymethylenes containing ethylene oxide as a comonomer.

Polyurethanes and polyureas.

Polycarbonate.

Polyamides and copolyamides derived from diamines and dicarboxylic acids and/or from aminocarboxylic acids or the corresponding lactams, such as polyamide 6, polyamide 6/6, polyamide 6/10, polyamide 11 or polyamide 12.

Polyesters derived from dicarboxylic acids and dialcohols and/or from hydroxycarboxylic acids or the corresponding lactones, such as polyethylene terephthalate, polybutylene terephthalate or poly-1,4-dimethylolcyclohexane terephthalate.

Crosslinked polymers derived from aldehydes on the one hand and from phenols, ureas and melamines on the other hand, such as phenol-formaldehyde resins, urea-formaldehyde resins and melamine-formaldehyde resins.

Finally, the new compounds can also be employed as stabilizers in the resins and lacquers field. Examples are thermosetting and thermoplastic acrylic resins which are used for coats of automobile lacquer (Encyclopedia of Polymer Science and Technology, Interscience Publishers, New York, Volume 1 (1964), pages 273–276, and Volume 13 (1970), pages 530–532; "Understanding Paint" by W. R. Fuller, in American Paint Journal Co., St. Louis, 1965, pages 124–135), acrylic resin lacquers, that is to say the customary stoving lacquers (described, for example, in H. Kittel's "Lehrbuch der Lacke und Beschichtungen" ("Textbook of Lacquers and Coatings"), Volume 1, Part 2, pages 735 and 742 (Berlin, 1972) and in H. Wagner and H. F. Sarx ("Lackkunstharze" ("Synthetic Resins for Lacquers"), pages 229–235) and very particularly mixtures based on an acrylic resin which can be crosslinked by heat and styrene and also lacquers and coatings based on an acrylic-melamine resin and an alkyl-acrylic/melamine resin. Lacquers of this type can contain, as further additives, other customary light stabilizers, phenolic antioxidants, pigments, dyestuffs, metal deactivators and the like.

A subject which is particularly important is the stabilization of polyolefins, styrene polymers, polyamides, poly-(meth)acrylates and polyurethanes, for which the compounds are preferentially suitable. Examples of this are polyethylene of high and low density, polypropylene, ethylene-propylene copolymers, polystyrene and styrene-butadiene-acrylonitrile terpolymers; mixtures of polyolefins or of styrene polymers and also polyurethanes based on polyethers or polyesters.

The new stabilizers are incorporated into the polymer composition by methods which are generally customary. The incorporation can be effected, for example, by mixing the compounds and, if desired, further additives into the melt by the methods customary in the art, before or during shaping, or by applying the compounds, dissolved or dispersed, to the polymer directly or by mixing the compounds into a solution, suspension or emulsion of the polymer, where appropriate with subsequent evaporation of the solvent. The quantities are 0.01 to 5, preferably 0.05 to 2.5 and, in particular, 0.1 to 1.0, % by weight, relative to the material to be stabilized. The new compounds can also be added to the plastics to be stabilized in the form of a master batch containing these compounds, for example in a concentration of 1 to 50, preferably 2.5 to 20, % by weight.

The plastics which have been stabilized by adding the substances according to the invention can, if appropriate, also contain other known and customary additives, such as, for example, antioxidants based on phenols and sulfides, metal deactivators and light stabilizers, phosphite stabilizers, metal compounds, epoxy stabilizers and polyhydric alcohols (see also German Offenlegungsschrift No. 2,427,853, pages 18–24).

Examples of antioxidants are sterically hindered phenols, such as 2,6-di-tert.-butyl-4-methylphenol, 4,4'-butylidene-bis-(2,6-di-tert.-butylphenol), 4,4'-thio-bis-(2-tert.-butyl-5-methylphenol), 2,5-di-tert.-butyl-4-hydroxyanisole, dioctadecyl 2,2-bis-(3,5-di-tert.-butyl-2-hydroxybenzyl)-malonate, 1,3,5-tris-(3,5-di-tert.-butyl-4-hydroxybenzyl)-2,4,6-trimethylbenzene, 2,4,6-tri-(3,5-di-tert.-butyl-4-hydroxybenzyl)-phenol, a phenolic triazine compound, such as 1,3,5-tris-(3,5-di-tert.-butyl-4-hydroxybenzyl) isocyanurate, esters of β-(3,5-di-tert.-butyl-4-hydroxyphenyl)-propionic acid with, for example, octadecanol, pentaerythritol and trishydroxyethyl isocyanurate, esters of 3,3-bis-(3-tert.-butyl-4-hydroxyphenyl)-butanoic acids with, for example, ethylene glycol, thiodipropionic acid esters with fatty alcohols, Ca or Ni salts of ethyl 3,5-di-tert.-butyl-4-hydroxybenzylphosphonate and dioctadecyl sulfide and disulfide.

The UV absorbers and light stabilizers include 2-(2'-hydroxyphenyl)-benztriazoles, such as, for example, the 5-chloro-3',5'-di-tert.-butyl derivative and the 5-chloro-3',5'-di-tert.-amyl derivative, 2-hydroxybenzophenones, such as, for example, the 4-heptoxy derivative or the 4-octoxy derivative, salicylates, such as octylphenyl salicylate, nickel complexes, such as, for example, the nickel complex of 2,2'-thio-bis-4-(1,1,3,3-tetramethylbutyl)-phenol and butylamine or other amines, oxalic acid diamides and sterically hindered amines.

Phosphites which may be mentioned are aliphatic, aromatic or aliphatic-aromatic phosphites, such as, for example, trisnonylphenyl phosphite, tris-(2,4-di-tert.-butylphenyl) phosphite, tris-(2-tert.-butylphenyl) phosphite or esters of pentaerythritol phosphite.

The following are examples of metal compounds which are known as stabilizers: calcium, barium, strontium, zinc, cadmium, magnesium, aluminum and lead soaps of aliphatic carboxylic acids or hydroxycarboxylic acids having about 12 to 32 C atoms, salts of the said metals with aromatic carboxylic acids, such as benzoates or salicylates, and (alkyl)-phenates of these metals, and also organotin compounds, such as, for example, dialkyltin thioglycolates and carboxylates.

Examples of known epoxy stabilizers are epoxidized higher fatty acids, such as epoxidized soya bean oil, tall oil or linseed oil, or epoxidized butyl oleate and also epoxides of long-chain olefins.

Polyhydric alcohols can, for example, be pentaerythritol, trimethylolpropane, sorbitol or mannitol, that is to say preferably alcohols having 5 or 6 C atoms and 2 to 6 OH groups.

An effective combination of stabilizers for poly-α-olefins, such as, for example, high-pressure, mediumpressure and low-pressure polymers of $C_2$ to $C_4$ α-olefins, in particular polyethylene and polypropylene, or copolymers of such α-olefins is composed, relative to 100 parts by weight of polymer, of, for example, 0.01 to 5 parts by weight of one of the compounds to be used in accordance with the invention, 0.05 to 5 parts by weight of a phenolic stabilizer, if appropriate 0.01 to 5 parts by weight of a co-stabilizer containing sulfur and, if appropriate, 0.01 to 3 parts by weight of a basic or neutral metal soap, such as, for example, calcium stearate or zinc stearate or the corresponding oxides, and, if appropriate, 0.01 to 5 parts by weight of a known UV stabilizer belonging to the group comprising the alkoxyhydroxybenzophenones, 4-hydroxyphenylbenztriazoles, benzylidenemalonic acid mononitrile esters or the so-called quenchers, such as, for example, nickel chelates. Plasticizers, lubricants, emulsifiers, fillers, such as, for example, chalk, talc or asbestos, pigments, optical brighteners, fire-proofing agents and antistatic agents may be regarded as examples of other customary additives.

The plastics which have been stabilized in accordance with the invention can be used in a wide variety of forms, for example as films, fibers, tapes or profiles or as binders for lacquers, adhesives or putties.

The examples below serve to illustrate the invention further.

I. PREPARATION OF ALCOHOLS BY PROCESS ROUTE (A)

EXAMPLE 1

2,7,7,9,9-Pentamethyl-2-isopropyl-8-(2,3-dihydroxypropyl)-1-oxa-4,8-diaza-spiro[4.5]decan-3-one 26.8 g (0.1 mole) of 2,7,7,9,9-pentamethyl-2-isopropyl-1-oxa-4,8-diaza-spiro[4.5]decan-3-one and 7.4 g (0.1 mole) of glycidol in 60 ml of hexanol were stirred for 65 hours at 140° C. in a stirring apparatus, using as catalyst 3 drops of concentrated HCl. The mixture was then evaporated on a rotary evaporator and the residue was recrystallized from xylene/methanol.

Yield: 25 g; melting point 183° C.

EXAMPLES 2 TO 5

The following were prepared from glycidol and other diazaspirodecanones as indicated in Example 1:

EXAMPLE 2

2,7,7,9,9-Pentamethyl-2-hexyl-8-(2,3-dihydroxypropyl)-1-oxa-3,8-diaza-spiro[4.5]decan-4-one; melting point 222° C.

EXAMPLE 3

2,2,7,7,9,9-Hexamethyl-8-(2,3-dihydroxypropyl)-1-oxa-3,8-diaza-spiro[4.5]decan-4-one; melting point 256° C.

EXAMPLE 4

2,2,4,4-Tetramethyl-3-(2,3-dihydroxypropyl)-7-oxa-3,14-dioxa-dispiro[5.1.5.2]pentadecan-15-one; melting point 257° C.

EXAMPLE 5

2,2,4,4-Tetramethyl-3-(2,3-dihydroxypropyl)-7-oxa-3,20-diaza-dispiro[5.1.11.2]heneicosan-21-one; melting point 208°-215° C.

EXAMPLE 6

7,7,9,9-Tetramethyl-2,2-dibenzyl-3-(2,3-dihydroxypropyl)-1-oxa-3,8-diaza-spiro[4.5]decan-4-one 39.2 g (0.1 mole) of 7,7,9,9-pentamethyl-2,2-dibenzyl-1-oxa-3,8-diaza-spiro[4.5]decan-4-one in 150 ml of n-propanol were initially taken. After adding 7.8 g (0.105 mole) of glycidol and 1 g of tricaprylmethylammonium chloride and 1 g of 50% strength sodium hydroxide solution as catalysts, the mixture was stirred for 16 hours at 80° C. and evaporated to dryness in vacuo, and the residue was pulverized, washed with water and dried.

Yield: 47 g; melting point 145° C.

EXAMPLES 7 TO 9

The following were prepared from glycidol and other diazaspirodecanones analogously to Example 6:

EXAMPLE 7

2,2,4,4-Tetramethyl-20-(2,3-dihydroxypropyl)-7-oxa-3,20-diaza-dispiro[5.1.11.2]heneicosan-21-one; melting point 124°-131° C.

EXAMPLE 8

7,7,9,9-Tetramethyl-2,2-diheptyl-3-(2,3-dihydroxypropyl)-1-oxa-3,8-diaza-dispiro[4.5]decan-4-one; melting point 95°-99° C.

EXAMPLE 9

7,7,9,9-Tetramethyl-2-isononyl-3-(2,3-dihydroxypropyl)-1-oxa-3,8-diaza-spiro[4,5]decan-4-one; resin

EXAMPLE 10

1,3,5-Tris-[2-hydroxy-3-(2,2,4,4-tetramethyl-7-oxa-3,20-diaza-21-oxo-disprio[5.1.11.2]heneicosyl-20)-propyl] isocyanurate 36.4 g (0.1 mole) of 2,2,4,4-tetramethyl-7-oxa-3,20-diaza-21-oxo-dispiro[5.1.11.2]heneicosane, 9.9 g (1/30 mole) of tris-[2,3-epoxypropyl] isocyanurate, 1 g of tricaprylmethylammonium chloride and 1 g of 50% strength NaOH in 100 ml of hexanol were stirred for 30 hours at 140° C. After cooling, the mixture was filtered, the filtrate was evaporated on a rotary evaporator, the residue was triturated with 200 ml of heptane and filtered off, and the solid was dried.

Yield: 35 g; melting point 155°-162° C.

EXAMPLES 11 TO 15

The following were prepared by the method described in Example 10:

EXAMPLE 11

1,4-Bis-[2-hydroxy-3-(2,2,4,4-tetramethyl-7-oxa-3,20-diaza-21-oxo-dispiro[5.1.11.2]heneicosyl-20)propoxy]-butane, using as starting materials the heneicosane employed in Example 10 and 1,4-bis-(2,3-epoxypropoxy)-butane.
Yield: 51 g; melting point 85°–92° C.

EXAMPLE 12

1,2,3-Tris-[2-hydroxy-3-(2,2,4,4-tetramethyl-7-oxa-3,20-diaza-21-oxo-dispiro[5.1.11.2]heneicosyl-20)-propoxyl-propane; from heneicosane and 1,2,3-tris-(2,3-epoxypropoxy)-propane.

Yield: 33 g; resin

EXAMPLE 13

1,2,3-Tris-[2-hydroxy-3-(2,2,7,7,9,9-hexamethyl-1-oxa-4,8-diazo-3-oxo-spiro[4.5]decyl-4)-propoxy]-propane;

using as starting materials 2,2,7,7,9,9-hexamethyl-1-oxa-4,8-diaza-spiro[4.5]decan-3-one and 1,2,3-tris-(2,3-epoxypropoxy)-propane in n-propanol as the solvent at 80° C.
Yield: 28 g; resin

EXAMPLE 14

1,4-Bis-[2-hydroxy-3-(2,7,7,9,9-pentamethyl-2-benzyl-1-oxa-3,8-diaza-4-oxo-spiro[4.5]decyl-3)-propoxy]-butane, using as starting materials 2,7,7,9,9-pentamethyl-2-benzyl-1-oxa-3,8-diaza-spiro[4.5]decan-4-one and 1,4-bis-(2,3-epoxypropoxy)-butane, analogously to Example 13.
Yield: 39 g; melting point 62°–65° C.

EXAMPLE 15

Bis-[2-hydroxy-3-(2,2,4,4,10,10,12-heptamethyl-7-oxa-3,14-diaza-15-oxo-dispiro[5.1.5.2]pentadecyl-14)-propyl]cyclohexane-1,2-dicarboxylate, using as starting materials 2,2,4,4,10,10,12-heptamethyl-7-oxa-3,14-diaza-dispiro[5.1.5.2]pentadecan-15-one and bis-(2,3-epoxypropyl) cyclohexane-1,2-dicarboxylate analogously to Example 13.
Yield: 44 g; melting point 130° C.

EXAMPLE 16

Bis-1,3-[2,2,4,4-tetramethyl-7-oxa-3,20-diaza-21-oxo-dispiro[5.1.11.2]heneicosyl-2-hydroxy]-propane 36.4 g (0.1 mole) of the heneicosane used in Example 10 in 300 ml of n-propanol containing 43.8 g of 2,2,4,4-tetramethyl-20-(2,3-epoxypropyl)-7-oxa-3,20-diaza-dispiro[5.1.11.2]heneicosan-21-one were stirred for 16 hours at 80° C., with the addition of the catalysts indicated in Example 10, in the same quantities. The mixture was filtered while hot and evaporated on a rotary evaporator and the residue was washed with water and dried.
Yield: 78 g of a colorless resin, melting point 107° C., molecular weight 784 by theory, 775 found.

EXAMPLE 17

7,7,9,9-Tetramethyl-2,2-diethyl-3,8-bis-(2,3-dihydroxypropyl)-1-oxa-3,8-diaza-spiro[4.5]decan-4-one 13.4 g (1/20 mole) of 7,7,9,9-tetramethyl-2,2-diethyl-1-oxa-3,8-diaza-spiro[4.5]decan-4-one, 3.7 g (1/20 mole) of glycidol and 1 drop of concentrated HCl in 60 ml of propanol were stirred for 10 hours at 80° C. A further 3.7 g of glycidol, 0.2 g of tricaprylmethylammonium chloride and 0.3 g of 50% strength NaOH were then added, after which the mixture was stirred for a further 15 hours at 80° C. The mixture was then filtered and the filtrate evaporated to dryness.
Yield: 20.7 g of a resin

II. PREPARATION OF ALCOHOLS BY PROCESS ROUTE (B)

EXAMPLE 18

2,7,7,9,9-Pentamethyl-2-ethyl-3-(2,3-dihydroxypropyl)-1-oxa-3,8-diaza-spiro[4.5]decan-4-one 50 g of 2,7,7,9,9-pentamethyl-2-ethyl-3-(2,3-epoxypropyl)-1-oxa-3,8-diaza-spiro[4.5]decan-4-one in 200 g of formic acid were boiled under reflux for 4 hours. The formic acid was removed by distillation in vacuo and the residue was boiled for 2 hours in 100 ml of 10% strength NaOH. An oily layer was formed, this was separated off and it solidified after a little time. The product was pulverized, washed with water and dried.
Yield: 45 g, melting point 121° C.

EXAMPLES 19 AND 20

The reaction was carried out as indicated in Example 18 and the following were obtained from the corresponding 2,3-epoxypropyl compounds:

EXAMPLE 19

7,7,9,9-Tetramethyl-2,2-diethyl-3-(2,3-dihydroxypropyl)-1-oxa-3,8-diaza-spiro[4.5]decan-4-one; melting point 104° C.

EXAMPLE 20

2,2,4,4-Tetramethyl-3-(2,3-dihydroxypropyl)-7-oxa-3,20-diaza-dispiro[5.1.11.2]heneicosan-21-one; melting point 126°–130° C.

III. PREPARATION OF SECONDARY PRODUCTS OF THE ALCOHOLS OBTAINED BY PROCESS ROUTE (A) OR (B)

EXAMPLE 21

Di-[bis-1,3-(2,2,4,4-tetramethyl-7-oxa-3,20-diaza-21-oxodispiro[5.1.11.2]heneicosyl)-2-propyl] succinate 15.7 g (0.02 mole) of the compound according to Example 16, 1.8 g (0.01 mole) of diethyl succinate and 0.1 g of LiNH$_2$ in 100 ml of absolute mesitylene were heated at 160° C., approx. 0.9 g of ethanol being distilled off in the course of 3 hours. The mixture was then concentrated to dryness and the residue was washed with water.
Yield: 15.7 g, melting point 129° C.

EXAMPLE 22

The reaction was carried out as in Example 21, but using 0.01 mole of diethyl sebacate.
Yield: 15.0 g, melting point 95° C.

EXAMPLES 23 TO 31

The following polyesters were prepared by the procedure of Example 21:

EXAMPLE 23

Starting from 0.015 mole of the compound according to Example 1 and 0.015 mole of dimethyl sebacate: 5.7 g of a solid resin, melting point approx. 70° C.

EXAMPLE 24

Starting from 0.02 mole of the compound according to Example 2 and 0.02 mole of diethyl malonate; 8.0 g of a solid resin, melting point 120°–137° C.

EXAMPLE 25

Starting from 0.02 mole of the compound according to Example 4 and 0.02 mole of dimethyl adipate: 7.6 g of a solid resin, melting point 94°–122° C.

EXAMPLE 26

Starting from 0.01 mole of the compound according to Example 10 and 0.01 mole of dimethyl suberate: 11.3 g of a solid resin, melting point 125°–139° C.

EXAMPLE 27

Starting from 0.01 mole of the compound according to Example 11 and 0.01 mole of diethyl malonate: 9.0 g of a solid resin, melting point 118°–142° C.

EXAMPLE 28

Starting from 0.01 mole of the compound according to Example 5 and 0.01 mole of diethyl succinate: 5.1 g of a solid resin, melting point 123°–142° C.

EXAMPLE 29

Starting from 0.01 mole of the compound according to Example 7 and 0.01 mole of diethyl malonate: 6 g, melting point 60°–78° C.

EXAMPLE 30

Starting from 0.01 mole of the compound according to Example 7 and 0.01 mole of dimethyl adipate: 6 g, melting point 51°–89° C.

EXAMPLE 31

Starting from 0.01 mole of the compound according to Example 17 and 0.01 mole of diethylmalonate: 4 g tacky resin.

EXAMPLE 32

A urethane was obtained in the following manner from the compound according to Example 10 and cyclohexyl isocyanate: 13.9 g (0.01 mole) of the compound according to Example 10 and 3.8 g (1/30 mole) of cyclohexyl isocyanate in 100 ml of toluene were stirred for 15 hours at 130° C. in the presence of 0.1 g of 1,4-diazinebicyclo[2.2.2]octane. The mixture was then evaporated to dryness. 17.3 g, melting point 110° C.

EXAMPLE 33

Starting from 0.02 mole of the compound according to Example 11 and 0.02 mole of hexamethylene diisocyanate, 21.4 g of a polyurethane of melting point 120°–136° C. were obtained analogously to Example 32.

EXAMPLE 34

This example demonstrates the volatility of the new triazine stabilizers compared with a product of the nearest state of the art.

The volatility figures were determined in an apparatus for thermogravimetric analysis. Equal quantities (500 mg) of the compounds according to the invention and of the comparison substance were heated to 300° C. in a nitrogen atmosphere at a speed of heating of 2K/minute, and the loss of substance was measured in mg/cm$^2$ of surface of the sample. The results are shown in the table below.

| Stabilizer according to Example | Loss of weight in mg/cm$^2$ on reaching a temperature of ... °C. | | | |
|---|---|---|---|---|
| | 220 | 260 | 300 | 10 minutes at 300° C. |
| 14 | 0.63 | 2.53 | 7.74 | 12.64 |
| 15 | 1.42 | 3.95 | 8.06 | 13.27 |
| Comparison* | 1.26 | 4.58 | 20.54 | 49.61 |
| Comparison** | 0.0 | 1.11 | 9.48 | 58.46 |

*Stabilizer according to Example 31 of German Offenlegungsschrift 2,606,026
**Stabilizer according to Example 1 of German Offenlegungsschrift 2,719,131

EXAMPLE 35

This example is intended to demonstrate the light-stabilizing action of the new compounds in poly-α-olefins.

100 parts by weight of polypropylene having a melt index i$_5$ (230° C.) of approx. 6 g/10 minutes (determined as specified in ASTM D 1238-62 T) and a density of 0.90 were mixed with 0.1 part by weight of pentaerythrityl tetrakis-3-(3,5-di-tert.-butyl-4-hydroxyphenyl)-propionate and 0.2 part by weight of calcium stearate and 0.1 part by weight of the stabilizer, according to the invention, to be tested.

In order to achieve the most uniform distribution possible on the polymer granules, the stabilizers were dissolved in a solvent, and the solution was added dropwise to the polypropylene powder, while stirring, the greater part of the solvent being re-evaporated by simultaneous irradiation using an IR lamp.

After approx. 20 minutes the calcium stearate was added and mixing was carried out for a further 10 minutes. Residues of solvent were removed by drying at 50° C. for 120 minutes in a drying cabinet.

The polypropylene was injection molded on a Windsor type SP 50 injection molding machine at 240° C. to give sheets measuring 60×60×1 mm. Test specimens as specified in DIN 53,455, mode 3, reduced in a ratio of 1:3, were punched out from these sheets. The test specimens required as comparison samples were prepared analogously, but omitting the stabilizer to be tested and/or adding the comparison stabilizers.

The stability to light was determined by subjecting the samples to irradiation with alternating light in a 1200 Xenotest apparatus made by Original Hanau Quarzlampen GmbH. The intensity of the radiation was modulated by UV filters (special filter glass, d=1.7 mm). The stability to light was tested as specified in DIN No. 53,387 (a dry period of 17 minutes, moistening for 3 minutes, a black-body temperature of 45° C. and a relative atmospheric humidity of 70 to 75% during the dry period). The elongation at break after a specific exposure time in hours was determined at a draw-off speed of 5 cm/minute on a tensile testing machine made by Instron.

| Stabilizer according to Example | Exposure time in hours | Elongation at break determined, as % of the initial value |
|---|---|---|
| 14 | 1,100 | 35 |
| 15 | 1,100 | 40 |
| Polypropylene | 260 | 1 |
| Comparison[1] | 320 | 1 |
| Comparison[2] | 600 | 1 |
| Comparison[3] | 1,100 | 1 |

[1] with no light stabilizer
[2] compound according to Example 1 of German Offenlegungsschrift 2,719,131
[3] compound according to Example 31 of German Offenlegungsschrift 2,606,026

EXAMPLE 36

A homogeneous mixture of polypropylene powder (®Hostalen PPU VP 1770 F made by Hoechst AG) of melt index MFI 190/3=1.9 g/10 minutes, see DIN No. 53,535, and the constituents of the formulation indicated below, was prepared in a high-speed laboratory mixer and was converted into granules. The material thus stabilized was then melted in a laboratory extruder under the customary processing conditions and was converted, via a spinning pump having an eight-orifice spinning nozzle, into monofilaments which were then subsequently stretched in a ratio of 1:3, texturized to give yarn of 40 dtex and processed to give test fabrics.

100 parts by weight of polypropylene, 0.2 part by weight of calcium stearate, 0.1 part by weight of ethylene glycol 3,3-bis-(3-tert.-butyl-4-hydroxyphenyl)-butanoate, 0.1 part by weight of dioctadecyl disulfide and 0.3 part by weight of the stabilizer to be tested.

The fabric samples were stretched on a perforated piece of cardboard in such a way that a free aperture of diameter approx. 15.5 mm was left. The test specimens were subjected to exposure in this form in the Xenotest X 1200 in accordance with the preceding example. At specific intervals of time, the fabric was loaded centrally with a weight of diameter 6 mm and a pressure of 0.1 N/mm². The point at which the weight breaks through was taken as the time of failure.

| Stabilizer according to Example | Exposure time in hours when the weight breaks through |
|---|---|
| 14 | >3100[4] |
| 15 | >3100[4] |
| Polypropylene | 280 |
| Comparison[1] | 400 |
| Comparison[2] | 1,400 |
| Comparison[3] | 3,000 |

[1] with no stabilizer
[2] compound according to Example 1 of German Offenlegungsschrift 2,719,131 (the commercial product Tinuvin 622)
[3] compound according to Example 31 of German Offenlegungsschrift 2,606,026
[4] weight had not broken through.

EXAMPLE 37

The stabilized granules which had been prepared as in the preceding Example were processed on a laboratory film blowing machine (screw diameter 25 mm, length 20 D) with a temperature program of 200°, 240°, 250° and 255° C. to give blown films having a thickness of approx. 70 μm. These films were subjected to artificial weathering as described in the Xenotest X 1200. The carbonyl number was determined as a criterion of damage, using a method based on DIN No. 53,383, Part 2. (This is defined for PP as the ratio of the extinction values at 1,715 cm⁻¹ and 1,524 cm⁻¹. The test specimen begins to disintegrate to powder at a CO number>2).

| Stabilizer according to Example | C = 0 number after ... hours | | | |
|---|---|---|---|---|
| | 500 | 1,000 | 2,000 | 2,500 |
| 14 | 0.1 | 0.2 | 0.9 | 1.2 |
| 15 | 0.1 | 0.2 | 0.8 | 1 |
| Polypropylene | >2 | — | — | — |
| Comparison[1] | >2 | — | — | — |
| Comparison[2] | — | >2 | — | — |
| Comparison[3] | 0.2 | 0.2 | 2 | — |

[1], [2] and [3] correspond to the comparison samples of the preceding Example.

EXAMPLE 38

100 g of a thermosetting acrylate clear lacquer (TSA) having a solids content of 40% by weight were mixed with 0.2 g of the stabilizer. The compatibility of the solution was examined visually.

| Stabilizer according to Example | Solubility |
|---|---|
| 14 | a clear, homogeneous solution |
| 15 | a clear, homogeneous solution |
| Comparison[3] | cloudy and inhomogeneous |

[3] corresponding to comparison sample 3 of Example 36.

We claim:

1. A compound of the general formula (I)

$$R^2-(A-\underset{R^1}{CH}-O-X^1-R^3-X^2)_n-E \qquad (I)$$

wherein n is an integer from 1 to 100, $X^1$ and $X^2$ are either identical and represent a bond or $$-\underset{}{\overset{O}{\underset{\|}{C}}}- \quad \text{or} \quad -\underset{}{\overset{H}{\underset{|}{N}}}-\underset{}{\overset{O}{\underset{\|}{C}}}-$$

in which n is 1, are different, in which case $X^2$ then has no meaning, $R^1$ is, if A is a group of formula (Va), hydrogen, $C_1$ to $C_{30}$ alkyl, phenyl or otherwise a group of the formula (IIa) or (IIb)

(IIa)     (IIb)

in which formulae Y is a radical $$\underset{O}{\overset{}{\underset{\|}{C}}}-N\diagdown \quad \text{or} \quad \diagup N-\underset{O}{\overset{}{\underset{\|}{C}}}$$

which occupies the ring positions 3,4, B is methylene, $R^4$ denotes hydrogen or methyl, $R^5$ and $R^6$ are identical or different and denote hydrogen, $C_1$ to $C_{18}$ alkyl, phenyl which is unsubstituted or substituted by chlorine or $C_1$ to $C_4$ alkyl, or $C_7$ to $C_{14}$ aralkyl which is unsubstituted or substituted by $C_1$ to $C_4$ alkyl, or, together with the carbon atom linking these radicals, form a $C_5$ to $C_{12}$ cycloalkyl ring which is unsubstituted or substituted by up to four $C_1$ to $C_4$ alkyl groups, or form a piperidine ring which is unsubstituted or substituted by up to four $C_1$- to $C_4$-alkyl groups, $R^7$ denotes a hydrogen atom or a $C_1$ to $C_4$ alkyl group and $R^2$ is, if $R^1$ denotes a group of formula (IIb) and A denotes a bonding or A is a group of formula (Va), hydrogen or $C_1$ to $C_{30}$ alkyl or phenyl, or otherwise a group of the formulae (II), or hydrogen in case of $A=-CH_2O-$, or a

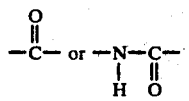

group which is substituted by $C_1$ to $C_{18}$ alkyl, $C_5$ or $C_6$ cycloalkyl or phenyl and which has

linked to A, or $C_2$ to $C_{18}$ alkylene, or phenylene which is unsubstituted or substituted by up to two $C_1$ to $C_4$ alkyl groups, or $C_7$ to $C_{14}$ aralkylene or $\alpha,\omega$-dicarboxy-$C_1$ to-$C_8$ alkylene or a dicarboxy-$C_6$ ring or a radical >N-alkyl having 1 to 6 C atoms or a group of the formula (III)

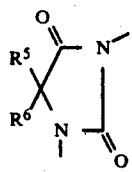

in which $R^5$ and $R^6$ have the meanings indicated above, or an isocyanuric acid radical or a nitrogen atom or a

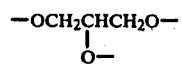

radical, $R^3$ represents hydrogen if $X^1$, $X^2$ and E have no meaning, or, if $X^2$ and E have no meaning, represents $C_1$ to $C_{18}$ alkyl or phenyl, which is unsubstituted or substituted by chlorine, hydroxyl, amino or $C_1$ to $C_4$ alkyl, $C_7$ to $C_{14}$ aralkyl or $C_5$ or $C_6$ cycloalkyl or denotes $C_2$ to $C_{12}$ alkylene or phenylene which is unsubstituted or substituted by one to four $C_1$ to $C_4$ alkyl groups, or denotes $C_7$ to $C_{14}$ aralkylene, A represents a bond or $-CH_2-$ or $-OCH_2-$ having $-O-$ linked to $R^2$, or a group of the formula (IV)

$$-O-\underset{\underset{Q}{|}}{CH_2CH_2}-B^1-R^8-B^1-CH_2- \quad (IV)$$

in which Q represents a radical (IIa) or (IIb), $B^1$ is a bond or $-O-$ and $R^8$ has the same meaning as $R^2$, free valences being saturated by the group

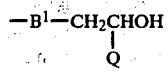

or A represents a group of the formula (Va)

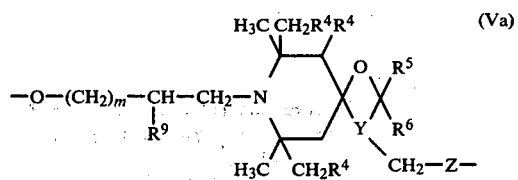

in which $R^4$, $R^5$, $R^6$ and Y have the meanings indicated above, Z is a bond or $-CH(OH)-$ and $R^9$ represents an OH group and has the meanings of $R^1$, and m is 0 or 1, in oligomeric or polymeric products in which $n>1$ $R^2$, as a terminal group, is hydrogen, $R^3$ is a bifunctional or trifunctional radical, from the group indicated for $R^3$ and A has the meaning of a bifunctional radical from the group indicated for A, and E is a group of the formula $R^2-A-CH(R^1)-O-$ wherein $R^1$, $R^2$ and A have the meanings indicated above, or E has no meaning, and at least in formula I one of the radicals $R^1$, $R^2$ or A contains a diazaspiradecane system of the formulae (II) or (V), or E is a terminal group which can be a lower alkyl ester, $-NCO$ or halogen.

2. A process for the preparation of compounds of the formula (I), which comprises either
(a) reacting a diazaspirodecane of the general formula (VIa) or (VIb)

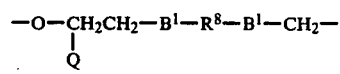

wherein $R^4$, $R^5$, $R^6$, $R^7$ and Y have the meanings indicated in claim 1, in the presence of a catalyst, at elevated temperatures and in an organic solvent, with 1.0 to 1.5 times the equivalent quantity of an epoxide of the formula (VIIa), $$R^2\!-\!(D\!-\!CH\overset{O}{\overset{\diagup\diagdown}{\text{———}}}CH_2)_n \quad (VIIa)$$

$R^2$ in formula (VIIa) having the meaning indicated in claim 1, and having additionally the meaning of a group of the formulae (II), n being 1, 2 or 3 and D representing a bond or methylene or $-OCH_2-$ in which $-O-$ is attached to $R^2$, after which, if desired, in order to prepare secondary products having a definite molecular weight, the alcohols thus obtained are also reacted in the presence of a catalyst and, if appropriate, an acid acceptor, at elevated temperatures and in a solvent, with an equivalent quantity, but, for the preparation of oligomeric or polymeric secondary products using an equimolar quantity, of a bifunctional compound of the formula (VIII)

$$R^3-(T)_m \qquad (VIII)$$

in which $R^3$ has the meaning indicated in claim 1, m is 1, 2 or 3 and T represents halogen, a lower alkyl ester, —COCl, —OH or —NCO, or (b) reacting a compound of the formula (VIIa) in which n=1, D=—CH$_2$— and $R^2$=a group of the formula (IIa) or (IIb) in which B represents a bond, at 100° C. with formic acid, which should be present in 3 to 10 times the molar quantity and acts at the same time as the solvent, then subjecting the ester which has been formed to alkaline saponification and, if desired, subjecting the alcohol obtained in this way to an oligomerization or a polymerization, as indicated above, with the addition of a compound of the formula (VIII).

3. A process for the stabilization of synthetic polymers against the harmful effect of light, which comprises adding to the polymers, if appropriate in addition to hitherto known substances having a stabilizing action, 0.01 to 5 parts by weight, relative to the polymer, of a stabilizer as claimed in claim 1.

4. Synthetic polymers which have been stabilized against UV light decomposition and which contain 0.01 to 5 parts by weight, relative to the polymer, of a stabilizer as claimed in claim 1.

* * * * *